(12) United States Patent
Burke et al.

(10) Patent No.: US 7,064,206 B1
(45) Date of Patent: *Jun. 20, 2006

(54) HIGHLY LIPOPHILIC CAMPTOTHECIN INTERMEDIATES AND PRODRUGS AND METHODS OF PREPARATION THEREOF

(75) Inventors: Thomas G. Burke, deceased, late of Lexington, KY (US); by Lori Latus, legal representative, Lexington, KY (US); Dennis P. Curran, Pittsburgh, PA (US); Wu Du, San Diego, CA (US)

(73) Assignees: University of Kentucky Research Foundation, Lexington, KY (US); University of Pittsburg, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/843,822

(22) Filed: May 12, 2004

Related U.S. Application Data

(60) Provisional application No. 60/469,805, filed on May 12, 2003.

(51) Int. Cl.
*C07F 7/10* (2006.01)
(52) U.S. Cl. ..................................... 546/14
(58) Field of Classification Search .................. 546/14
See application file for complete search history.

(56) References Cited

U.S. PATENT DOCUMENTS

| | | |
|---|---|---|
| 5,552,156 A | 9/1996 | Burke |
| 5,736,156 A | 4/1998 | Burke |
| 6,136,978 A | 10/2000 | Curran et al. |
| 6,207,832 B1 | 3/2001 | Curran et al. |
| 6,291,676 B1 | 9/2001 | Burke et al. |
| 6,376,676 B1 | 4/2002 | Curran et al. |
| 6,410,731 B1 | 6/2002 | Currant et al. |
| 6,743,917 B1 | 6/2004 | Curran et al. |

OTHER PUBLICATIONS

Josien, H. 7-Silylcamptothecins (Silatecans): A New Family of Camptothecin Antitumor Agents, Bioorg. Med. Chem. Lett. 7(24), pp. 3189-3194 (1997).*

Liu, X. A Versatile Prodrug Approach for Liposomal Core-Loading of Water-Insoluble Camptothecin Anticancer Drugs, J. Amer. Chem. Soc., 124, pp. 7650-7651 (2002).*

Josien, H., et al., Bioorganic & Medicinal Chemistry Letters, vol. 7, pp. 3189-3194 (1997).*

Liu, Xinli et al., A Versatile Prodrug Approach for Liposomal Core-Loading of Water-Insoluble Camptothecin Anticancer Drugs; J. Am. Chem. Soc.; Jan. 16, 2002, 124, 7650-7651.

Curran, D.P. Liu, H.; Josien, H; Ko, S.B., Tandem Radical Reactions of Isonitriles with 2-Pyridonyl and other aryl radicals: Scope and Limitations, and a First Generation Synthesis of (+/−)-Camptothecin, Tetrahedron, 52, 11385-11404 (1996). Published Aug. 1996.

Palmisano, F. et al., Determination of Methotrexate in Untreated Body Fluids by Micellar Liquid Chromatography, Anal. Chem., May 1989, (61) 946-950.

Pinnaduwage, P. et al. Stable Target-Sensitive Immunoliposomes, Biochemistry, 32, pp. 2850-2855 1992.

Mi, Z. and Burke, T.G., Differential Interactions of Camptothecin Lactone and Carboxylate Forms with Human Blood Components, Biochemistry, 33, 10325-10336 (1994).

Mi, Z. and Burke, T.G., Marked Interspecies Variations Concerning the Interactions of Camptothecin with Serum Albumins: A Frequency-Domain Fluorescence Spectroscopic Study, Biochemistry, 33, 12540-12545 (1994).

Mi, Z. et al., Reduced Albumin Binding Promotes the Stability and Activity of Topotecan in Human Blood, Biochemistry, 34, 13722-13727 (1995).

Josien, H. et al., 7-Silylcamptothecins (Silatecans): A New Family of Camptothecin Antitumor Agents, Bioorg. Med. Chem. Lett. vol. 7, No. 24, 3189-3295 (1997).

Josien, H. et al., A General Synthetic Approach to the (20S)-Camptothecin Family of Antitumor Agents by a Regiocontrolled Cascade Radical Cyclization of Aryl Isonitrites, Chem. Eur. J. 4, 67-83 (1998).

Curran, D.P. et al., New 4+1 Radical Annulations: A Formal Total Synthesis of (+/−)-Camptothecin, J. Am. Chem. Soc., 114, 5863-5864 (1992).

(Continued)

*Primary Examiner*—Kamal A. Saeed
*Assistant Examiner*—Nyeemah Grazier
(74) *Attorney, Agent, or Firm*—King & Schickli, PLLC

(57) ABSTRACT

The present invention relates to novel, highly lipophilic silatecan intermediates and prodrugs of DB-67 and other silatecans.

2 Claims, No Drawings

OTHER PUBLICATIONS

Burke, T. et al., Liposomal Stabilization of Camptothecin's Lactone Ring, J. Am. Chem. Soc., 114, 8318-8319 (1992).

Margali, R. et al., Liposomal Drug Delivery: Thermodynamic and Chemical Kinetic Considerations, J. Controlled Release, vol. 17, 285-296 (1991).

Akhtar, et al., Liposome delivery of Antisense Oligonucleotides: Adsorption and Efflux characteristics of Phosphorothioate Oligodeoxynucleotides, J. Controlled Release 22 (1992) 47-56.

Hong, C. et al., Nucleoside Conjugates. 11. Synthesis and Antitumor Activity of 1- -D-Arabinofuranosylcytosine and Cytidine Conjugates of Thioether Lipids, J. Med. Chem., 1990, 33, 1380-1386.

Burke, T.G. et al., The Structural Basis of Camptothecin Interactions with Human Serum Albumin: Impact on Drug Stability, J. Med. Chem., 37, 40-46 (1994).

Bom, D. et al., Novel A,B,E-Ring-Modified Camptothecins Displaying High Lipophilicity and Marked Improved Human Blood Stabilities, J. Med. Chem. 42, 3018-3022, 1999.

Killion, J. et al., Augmentation of Antiproliferative Activity of Interferon Alfa Against Human Bladder Tumor Cell Lines by Encapsulation of Interferon Alfa Within Liposomes, J. Natl. Cancer Inst. 81, 1387-1392 (1989).

Rahman, A. et al., Anti-Laminin Receptor Antibody Targeting of Liposomes with Encapsulated Doxorubicin to Human Breast Cancer Cells in Vitro, J. Natl. Cancer Inst. 81, 1794-1800 (1989).

Burris, H. et al. Activity of Topotecan, a New Topoisinerase I Inhibitor, Against Human Tumor Colony-Forming Units In Vitro, J. Natl. Cancer Inst. 84, 1816-1820 (1992).

Jett, M. et al., Tumoricidal Effects of Liposomes Containing Phosphatidylinositol or Phosphatidylcholine, Methods in Enzymology, vol. 141, pp. 459-466 (1987).

Woodle, M. et al., Liposome Preparation and Size Characterization, Methods in Enzymology, vol. 171, pp. 193-217 (1989).

Szoka, F. et al., Procedure for Preparation of Liposomes with Large Internal Aqueous Space and High Capture by Reverse-Phase Evaporation, Proc. Nat. Acad. Sci., vol. 75, 4194-4198. (Sep. 1978).

Gabizon, A. et al., Liposome Formulations with Prolonged Circulation Time in Blood and Enhanced Uptake by Tumors, Proc. Natl. Acad. Sci. 85, 6949-6953, Sep. 1988.

Papahadjopoulos et al., Sterically Stabilized Liposomes: Improvements in Pharmacokinetics and Antitumor Therapeutic Efficacy, Proc. Natl. Acad. Sci. 88, 11460-11464, Dec. 1991.

Shelly, K. et al., Model Studies Directed Toward the Boron Neutron-Capture Therapy of Cancer: Boron Delivery to Murine Tumors with Liposomes, Proc. Natl. Acad. Sci. vol. 89, 9039-9043, Oct. 1991.

Giovanella, B. et al., DNA Topoisomerase I-Targeted Chemotherapy of Human Colon Cancer in Xenografts, Science 246, 1046-1048, Nov. 24, 1989.

Josien, H. et al, Synthesis of (S)-Mappicine and Mappicine Ketone Via Radical Cascade Reaction of Isonitriles, Tetrahedron, 53, 8881-8886 (1997).

Jew et al., Synthesis and Antitumor Activity of 7-Substituted 20(RS)-Camptothecin Analogues, Bioorg. Med. Chem. Letters 6, 845-848.

Wang et al., Synthesis of Novel Water-Soluble 7-(aminoacylhydrazono) -formyl Camptothecins with Potent Inhibition of DNA Topo. I, Bioorg. Med. Chem. 2(12), 1397-1402 (1994).

Wang et al., Novel Water-Soluble 7-(acylhydrazono) -formyl Camptothecins as Potent Inhibitors of DNA Topo, I, Bioorg. Med. Chem. Lett. 4(4), 579-582 (1994).

Sawada et al., Chem. Mod. of an Antitumor Alkaloid Camptothecin: Synthesis and Antitumor Activity of 7-C-Sub. Camptothecs; Chem. Pharm. Bull. 39(10), 2574-80(1991).

* cited by examiner

HIGHLY LIPOPHILIC CAMPTOTHECIN INTERMEDIATES AND PRODRUGS AND METHODS OF PREPARATION THEREOF

This application claims the benefit of U.S. Provisional Patent Application Ser. No. 60/469,805 filed on May 12, 2003.

This invention was made with Government support under NIH Grant Number 1R01CA63653. The Government may have certain rights in this invention.

nicks are converted to irreversible and lethal double strand DNA breaks during replication.

The camptothecin class of anticancer agents have exhibited unusual reactivity in vivo, both with respect to drug hydrolysis and blood protein interactions. These factors have hindered the pharmaceutical development and clinical implementation of camptothecins. In terms of hydrolysis, each of the camptothecins shown in Table 1 contains an α-hydroxy-δ-lactone pharmacophore.

TABLE 1

Clinical candidates and FDA-approved analogs in the camptothecin family of antitumor agents

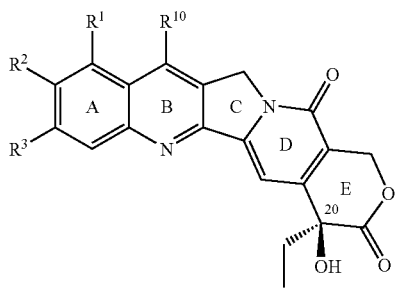

| Aqueous Solubility | Compound | $R^{10}$ | $R^1$ | $R^2$ | $R^3$ |
|---|---|---|---|---|---|
| Soluble | Topotecan/TPT | H | $CH_2NH(CH_3)_2$ | OH | H |
| " | CDK602 | H | $C_2H_5NHCH(CH_3)_2$ | H | H |
| " | Irinotecan/CPT-11 | $C_2H_5$ | H | [piperidine-piperidine-carbamate group] | H |
| " | GI-147211C/GG-211 | $-CH_2-N\underset{}{\diagdown}N-CH_3$ | H | | [dioxolane group] |
| Insoluble | Camptothecin | H | H | H | H |
| " | 9-AC | H | $NH_2$ | H | H |
| " | 9-NC/Rubitecan | H | $NO_2$ | H | H |
| " | SN-38 | $C_2H_5$ | H | OH | H |
| " | DB-67 | $Si(CH_3)_2C(CH_3)_3$ | H | OH | H |
| " | MDCPT | H | H | | [methylenedioxy group] |

TECHNICAL FIELD

The present invention relates to novel intermediates and prodrugs of highly lipophilic 7-silylalkylcamptothecins (silatecans).

BACKGROUND OF THE INVENTION

Camptothecin and related analogs (Table 1) are emerging as a prominent class of agents useful in the treatment of cancer. The camptothecins display a unique mechanism of action: stabilization of the covalent binding of the enzyme topoisomerase I (topo I), an intranuclear enzyme that is overexpressed in a variety of tumor lines, to DNA. This drug/enzyme/DNA complex leads to reversible, single strand nicks. According to the fork collision model, the DNA At physiological pH of 7 and above this functionality is reactive, readily converting to the biologically inactive "ring opened" carboxylate form. Thus, as a result of the labile α-hydroxy-δ-lactone pharmacophore, an equilibrium is established between two distinct drug species: 1) the biologically active lactone form where the lactone ring remains closed; and 2) a biologically-inactive carboxylate form generated upon the hydrolysis of the lactone ring of the parent drug.

This hydrolysis problem with camptothecin and many analogs (e.g. 9-aminocamptothecin, 9-nitrocamptothecin) is exacerbated in human blood. In human blood and tissues, the camptothecin equilibrium of active lactone form vs. inactive carboxylate form can be strongly modulated by the presence of human serum albumin (HSA). The lactone form of camptothecin binds to HSA with moderate affinity yet the carboxylate form of camptothecin binds much more tightly than the carboxylate, displaying the 150-fold enhancement in its affinity. Thus, the preferential binding of the carboxylate form to HSA drives the equilibrium to the right in favor of the carboxylate, resulting in the lactone ring hydrolyzing more rapidly and completely (than when camptothecin is in an aqueous solution without HSA).

The development of 7-silylcamptothecins (or silatecans) has resulted in the identification of agents with improved human blood stabilities and activities. Recent rational design efforts have resulted in the identification of A,B-ring modified camptothecins displaying improved human blood stabilities combined with potent anti-topoisomerase I activities. Dual 7,10-substitution (where the 10-substituent is a hydroxy group) results in camptothecins displaying vastly improved human blood stabilities. SN-38 contains this dual 7-alkyl-10-hydroxy substitution pattern and in 1994 it was shown that these structural modifications block SN-38 from associating with the high affinity camptothecin carboxylate binding pocket on HSA.

More recently the design of another dual 7,10-modified camptothecin has been described. The new agent is 7-t-butyldimethylsilyl-10-hydroxycamptothecin (DB-67). DB-67 displays markedly improved human blood stability and potent anti-topoisomerase I anticancer activity. The design of DB-67 was based upon the following two considerations: 1) dual 7,10-substitution patterns eliminate the highly specific binding of carboxylate form over lactone form by HSA; and 2) lactone stabilization is further promoted by enhanced lipophilicity or lipid bilayer partitioning. Lipophilicity promotes camptothecin drug stability by favoring lactone partitioning into blood cells, thereby protecting the active lactone forms from hydrolysis. The key α-hydroxy-δ-lactone pharmacophore in DB-67 displays superior stability in human blood when compared with FDA-approved topotecan, CPT-11, and several other clinically relevant camptothecin analogs. DB-67 displayed a $t_{1/2}$ of 130 min. and a % lactone at equilibrium value of 30 in human blood; the t-butyldimethylsilyl group enhances lipophilicity and thereby promotes drug associations with blood cells. DB-67 is 25 times lipophilic than camptothecin and readily incorporates as its active lactone form into cellular and liposomal bilayers. Equally important, the dual 7-alkyl-silyl and 10-hydroxy substitution in DB-67 blocks the associations of the carboxylate form of DB-67 with the high affinity carboxylate binding pocket on HSA. Together, the enhanced lipophilicity and altered HSA interactions provide DB-67 with the highest human blood stability when compared with clinically relevant camptothecins containing the conventional α-hydroxy-δ-lactone pharmacophore.

In vitro cytotoxicity assays have shown that DB-67 is of comparable potency relative to camptothecin and 10-hydroxycamptothecin, as well as the FDA approved analogs topotecan and CPT-11. In addition, cell-free cleavage assays reveal that DB-67 forms more stable topoisomerase I cleavage complexes than camptothecin or SN-38. In terms of in vitro potency, DB-67 has been shown to display activity against human glioma in a murine model. Overall, these stability and activity profiles of DB-67 indicate how rational drug design can result in new, highly lipophilic agents displaying improved pharmacological properties.

In this invention we describe novel, highly lipophilic intermediates and prodrugs of DB-67 and other silatecans.

DETAILED DESCRIPTION OF THE INVENTION

Our previous rational synthetic efforts described above yielded a series of silatecan agents. 7-t-Butyldimethylsilyl-10-hydroxycamptothecin, which we have termed DB-67, is an example of a silatecan that displays improved biological properties. In the current invention we describe novel intermediates and prodrugs of DB-67 and related 7-silylcamptothecins or silatecans.

The invention includes compounds with the following structures A and B:

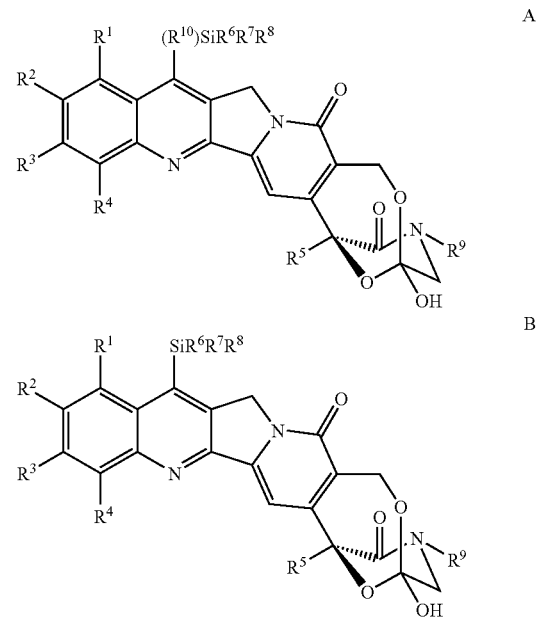

wherein $R^1$ and $R^2$ are independently the same or different and are hydrogen, an alkyl group, an alkenyl group, an alkynyl group, an alkoxy group, an aryloxy group, an acyloxy group, $OC(O)OR^{12}$ wherein $R^{12}$ is an alkyl group, a carbamoyloxy group, a halogen, a hydroxy group, a nitro group, a cyano group, an azido group, a formyl group, a hydrazino group, $C(O)R^{13}$ wherein $R^{13}$ is an alkyl group, an alkoxy group, an amino group or a hydroxy group, $SR^{14}$, wherein $R^{14}$ is hydrogen, $C(O)R^{13}$, an alkyl group, or an aryl group; or $R^1$ and $R^2$ together form a group of the formula $O(CH_2)_pO$ wherein p represents an integer 1 through 6; $R^3$ is H, a nitro group, a halogen atom, an amino group, a hydroxy group, or a cyano group, or $R^2$ and $R^3$ together form a group of the formula $O(CH_2)_pO$ wherein p represents an integer 1 through 6; $R^4$ is H, F, an alkyl group, an alkenyl group, an alkynyl group, a trialkylsilyl group or an alkoxy group; $R^5$ is a $C_{1-15}$ alkyl group, an allyl group, a benzyl group or a propargyl group; $R^6$, $R^7$ and $R^8$ are independently a $C_{1-15}$ alkyl group, a $C_{2-15}$ alkenyl group, a $C_{2-15}$ alkynyl group, an aryl group or a $(CH_2)_qR^{15}$ group, wherein q is an integer between 1 and 15 and $R^{15}$ is a hydroxy group, alkoxy group, an amino group, an alkylamino group, a dialkylamino group, a halogen atom, a cyano group or a nitro group; $R^9$ is a hydrogen, an alkyl group, an alkenyl group, an alkynyl group, an alkoxy group, an aryloxy group, or an acyloxy group; $R^{10}$ is an alkylene group, an alkenylene group or an alkynylene group.

The invention also includes compounds with the following structures C and D:

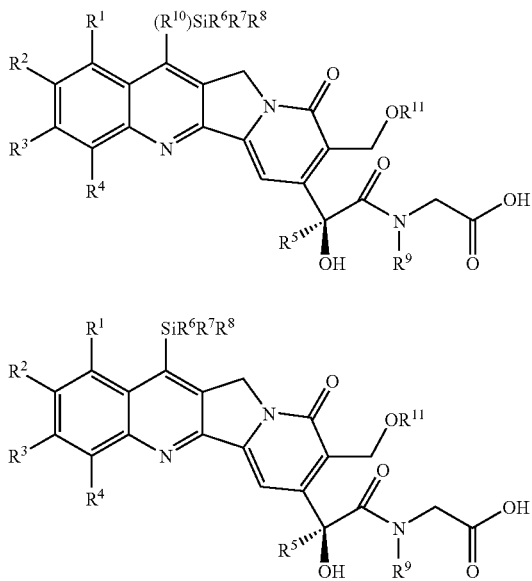

wherein R¹ and R² are independently the same or different and are hydrogen, an alkyl group, an alkenyl group, an alkynyl group, an alkoxy group, an aryloxy group, an acyloxy group, OC(O)OR¹² wherein R¹² is an alkyl group, a carbamoyloxy group, a halogen, a hydroxy group, a nitro group, a cyano group, an azido group, a formyl group, a hydrazino group, C(O)R¹³ wherein R¹³ is an alkyl group, an alkoxy group, an amino group or a hydroxy group, SR¹⁴, wherein R¹⁴ is hydrogen, C(O)R¹³, an alkyl group, or an aryl group; or R¹ and R² together form a group of the formula O(CH₂)$_p$O wherein p represents an integer 1 through 6; R³ is H, a nitro group, a halogen atom, an amino group, a hydroxy group, or a cyano group, or R² and R³ together form a group of the formula O(CH₂)$_p$O wherein p represents an integer 1 through 6; R⁴ is H, F, an alkyl group, an alkenyl group, an alkynyl group, a trialkylsilyl group or an alkoxy group; R⁵ is a C$_{1-15}$ alkyl group, an allyl group, a benzyl group or a propargyl group; R⁶, R⁷ and R⁸ are independently a C$_{1-15}$ alkyl group, a C$_{2-15}$ alkenyl group, a C$_{2-15}$ alkynyl group, an aryl group or a (CH₂)$_q$R¹⁵ group, wherein q is an integer between 1 and 15 and R¹⁵ is a hydroxy group, alkoxy group, an amino group, an alkylamino group, a dialkylamino group, a halogen atom, a cyano group or a nitro group; R⁹ is a hydrogen, an alkyl group, an alkenyl group, an alkynyl group, an alkoxy group, an aryloxy group, or an acyloxy group; R¹⁰ is an alkylene group, an alkenylene group or an alkynylene group; R¹¹ is (CH₂)$_L$NR¹⁶R¹⁷ wherein L may be an integer ranging from 1–30 and R¹⁶ and R¹⁷ are independently the same or different and are hydrogen, a C$_{1-15}$ alkyl group, a C$_{2-15}$ alkenyl group, a C$_{2-15}$ alkynyl group, an aryl group, a (CH₂)$_Y$R¹⁸ group, a (CH₂)$_Y$C(O)R¹⁸ group or a (CH²)$_Y$CO₂R¹⁸ wherein Y may be an integer ranging from 1 to 15 and R¹⁸ is a hydroxy group, a thiol group, an alkylthiol, a silyl group, an alkoxy group, an amino group, an alkylamino group, a dialkylamino group, a halogen atom, a cyano group, a nitro group. R¹¹ may also be a hydrogen, an alkyl group, an alkenyl group.

All compounds of the present invention including the β-hydroxylactone group can exist in racemic form, enantiomerically enriched from, and enantiomerically pure form.

The formulas of such compounds as set forth herein cover and/or include each such form.

The terms "alkyl", "aryl" and other groups refer generally to both unsubstituted and substituted groups unless specified to the contrary. Unless otherwise specified, alkyl groups are hydrocarbon groups and are preferably C$_1$–C$_{15}$ (that is, having 1 to 15 carbon atoms) alkyl groups, and more preferably C$_1$–C$_{10}$ alkyl groups, and can be branched or unbranched, acyclic or cyclic. The above definition of an alkyl group and other definitions apply also when the group is a substituent on another group (for example, an alkyl group as a substituent of an alkylamino group or a dialkylamino group). The term "aryl" refers to phenyl or napthyl. As used herein, the terms "halogen" or "halo" refer to fluoro, chloro, bromo and iodo.

The term "alkoxy" refers to —OR$^d$, wherein R$^d$ is an alkyl group. The term "aryloxy" refers to —OR$^e$, wherein R$^e$ is an aryl group. The term acyl refers to —C(O)R$^f$. The term "alkenyl" refers to a straight or branched chain hydrocarbon group with at least one double bond, preferably with 2–15 carbon atoms, and more preferably with 2–10 carbon atoms (for example, —CH=CHR$^g$ or —CH₂CH=CHR$^g$). The term "alkynyl" refers to a straight or branched chain hydrocarbon group with at least one triple bond, preferably with 2–15 carbon atoms, and more preferably with 2–10 carbon atoms (for example, —C≡CR$^h$ or —CH²C≡CR$^h$). The terms "alkylene," "alkenylene" and "alkynylene" refer to bivalent forms of alkyl, alkenyl and alkynyl groups, respectively.

The groups set forth above, can be substituted with a wide variety of substituents to synthesize homocamptothecin analogs retaining activity. For example, alkyl groups may preferably be substituted with a group or groups including, but not limited to, a benzyl group, a phenyl group, an alkoxy group, a hydroxy group, an amino group (including, for example, free amino groups, alkylamino, dialkylamino groups and arylamino groups), an alkenyl group, an alkynyl group and an acyloxy group. In the case of amino groups (—NR$^a$R$^b$), R$^a$ and R$^b$ are preferably independently hydrogen, an acyl group, an alkyl group, or an aryl group. Acyl groups may preferably be substituted with (that is, R$^f$ is) an alkyl group, a haloalkyl group (for example, a perfluoroalkyl group), an alkoxy group, an amino group and a hydroxy group. Alkynyl groups and alkenyl groups may preferably be substituted with (that is, R$^g$ and R$^h$ are preferably) a group or groups including, but not limited to, an alkyl group, an alkoxyalkyl group, an amino alkyl group and a benzyl group.

The term "acyloxy" as used herein refers to the group —OC(O)R$^d$.

The term "alkoxycarbonyloxy" as used herein refers to the group —OC(O)OR$^d$.

The term "carbamoyloxy" as used herein refers to the group —OC(O)NR$^a$R$^b$.

Amino and hydroxy groups may include protective groups as known in the art. Preferred protective groups for amino groups include tert-butyloxycarbonyl, formyl, acetyl, benzyl, p-methoxybenzyloxycarbonyl, trityl. Other suitable protecting groups as known to those skilled in the art are disclosed in Greene, T., Wuts, P. G. M., *Protective Groups in Organic Synthesis*, Wiley (1991), the disclosure of which is incorporated herein by reference.

In general, R¹, R² and R³ are preferably not excessively bulky to maintain activity of the resultant camptothecin analog. Preferably, therefore, R¹, R² and R³ independently have a molecular weight less than approximately 250. More preferably R¹, R² and R³ independently have a molecular weight less than approximately 200.

Some of the camptothecin analogs of the present invention can be prepared for pharmaceutical use as salts with inorganic acids such as, but not limited to, hydrochloride, hydrobromide, sulfate, phosphate, and nitrate. The camptothecin analogs can also be prepared as salts with organic acids such as, but not limited to, acetate, tartrate, fumarate, succinate, citrate, methanesulfonate, p-toluenesulfonate, and stearate. Other acids can be used as intermediates in the preparation of the compounds of the present invention and their pharmaceutically acceptable salts.

For purification, administration or other purposes, the E-ring (the lactone ring) may be opened with alkali metal such as, but not limited to, sodium hydroxide or calcium hydroxide, to form opened E-ring analogs of compounds of the present invention. The intermediates thus obtained are more soluble in water and may be purified to produce, after treatment with an acid, a purified form of the camptothecin analogs of the present invention.

All the novel compounds of the present invention whether in racemic, enantiomerically enriched or enantiomerically pure form display good biological activity while also possessing favorable characteristics for active loading into liposomal particle drug delivery systems of the micelle type disclosed and described in U.S. Pat. Nos. 5,316,771; 5,552,156 and 5,736,156. Pre-made liposomes can be efficiently loaded with any of the novel compounds of this invention using pH gradients.

In brief, in the active core loading process an amine-containing agent is loaded into the particle. For example, a gradient created by ammonia gas diffusing out of the liposome particle can result in diffusion or active loading of the compound/agent of the present invention inward to the core of the particle. The chemical gradient across the membrane creates a driving force for the compound/agent to replace the lost $NH_3$ from the interior of the liposome. Once inside the acidic confines of the core, the compound/agent becomes protonated and remains within the core, as its positive charge impedes retro-diffusion across the liposome bilayer. The protonated amine also prevents the occurrence of nucleophilic attack of the amine on the lactone carbonyl. As liposomes can be actively and/or passively targeted to the tumor, the liposome encapsulated compound/agent can be effectively concentrated at the tumor site, therby reducing exposure of the healthy host tissues to the cytotoxic agent yet enhancing exposure at the tumor target.

The tumor targeted approach involving liposomal delivery of core loaded compound/agent addresses multiple clinical issues. For example, reduced systemic toxicity can be achieved. Enhanced exposure at the tumor site in terms of relative amounts of drug reaching the tumor can also be achieved. Furthermore, enhanced exposure at the tumor site can be achieved in terms of prolonging the exposure of drug there.

The present invention also provides a method of treating a patient, which comprises administering a pharmaceutically effective amount of a compound of the present invention. The compound may, for example, be administered to a patient afflicted with cancer and/or leukemia. The compounds of the present invention may also act as antiviral (for example, anti-HIV) agents and antiparasitic agents. The pharmaceutically effective amount or dosage is preferably between 0.01 to 80 mg of one of the compounds of structures A, B and/or C per kg of body weight. More preferably, the pharmaceutically effective amount or dosage is preferably between 0.1 to 40 mg of one or more of the compounds per kg of body weight. In general, a pharmaceutically effective amount or dosage contains an amount of one of the compounds effective to display antileukemic and/or antitumor (anticancer) behavior. Pharmaceutical compositions containing as an active ingredient of one of the compounds of the present invention including a pharmaceutically acceptable salt thereof in association with a pharmaceutically acceptable carrier or diluent are also within the scope of the present invention.

The novel compounds of the present invention display good biological activity while also possessing favorable characteristics for active loading into liposomal particle drug delivery systems of the micelle type disclosed and described in U.S. Pat. Nos. 5,316,771; 5,552,156 and 5,736,156. Pre-made liposomes can be efficiently loaded with the novel compounds of this invention using pH gradients.

In brief, in the active core loading process an amine-containing agent is loaded into the particle. For example, a gradient created by ammonia gas diffusing out of the liposome particle can result in diffusion or active loading of the compound/agent of the present invention inward to the core of the particle. The chemical gradient across the membrane creates a driving force for the compound/agent to replace the lost $NH_3$ from the interior of the liposome. Once inside the acidic confines of the core, the compound/agent becomes protonated and remains within the core, as its positive charge impedes retro-diffusion across the liposome bilayer. The protonated amine also prevents the occurrence of nucleophilic attack of the amine on the lactone carbonyl. As liposomes can be actively and/or passively targeted to the tumor, the liposome encapsulated compound/agent can be effectively concentrated at the tumor site, therby reducing exposure of the healthy host tissues to the cytotoxic agent yet enhancing exposure at the tumor target.

The tumor targeted approach involving liposomal delivery of core loaded compound/agent addresses multiple clinical issues. For example, reduced systemic toxicity can be achieved. Enhanced exposure at the tumor site in terms of relative amounts of drug reaching the tumor can also be achieved. Furthermore, enhanced exposure at the tumor site can be achieved in terms of prolonging the exposure of drug there.

The compounds of the present invention may be administered in a dose which is effective at inhibiting the enzyme topoisomerase I. These amounts are generally from about 1–80 mg/kh of body weight per week, preferably about 2–40 mg/kg per week.

The compounds of the present invention may be administered as a pharmaceutical composition containing the compounds and a pharmaceutically acceptable carrier or diluent. The compounds can be administered as their ring open salt forms, since relactonization to their active forms can occur in the body (especially at sites of reduced pH). The active material can also be mixed with other active materials which do not impair the desired action and/or supplement the desired action. The compounds/active materials according to the present invention can be administered by any route, for example, orally, nasally, parenterally, intravenously, intradermally, subcutaneously, or topically, in liquid or solid form.

For the purposes of parenteral therapeutic administration, the active ingredient may be incorporated into a solution or suspension. The solutions or suspensions may also include the following components: a sterile diluent such as water: for injection, suspensions of liposomal particles whereby the particles contain stable, active drug within the core of the particle in a pH controlled and protected environment or associated to the outside of the particle or any of the bilayers of the particle, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

Another mode of administration of the compounds of this invention is oral. Oral compositions will generally include an inert diluent or an edible carrier. They may be enclosed in gelatin capsules or compressed into tablet. For the purpose of oral therapeutic administration, the aforesaid compounds may be incorporated with excipients and used in the form of tablets, troches, capsules, elixirs, suspensions, syrups, wafers, chewing gums and the like.

The tablets, pills, capsules and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such a colloidal silicon dioxide; and a sweetening agent such as sucrose or saccharin or flavoring agent such as peppermint, methyl salicylate, or orange flavoring may be added. When the dosage unit is in the form of a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and coloring and flavors. Materials used in preparing these various compositions should be pharmaceutically or veterinarally pure and non-toxic in the amount used.

The following examples are presented to further illustrate the invention, but it is not to be considered as limited thereto.

EXAMPLE 1

Preparation of DB-67 20(S) ω-aminoalkanoanic esters

DB-67 ω-aminoalkanoanic esters were synthesized as following:

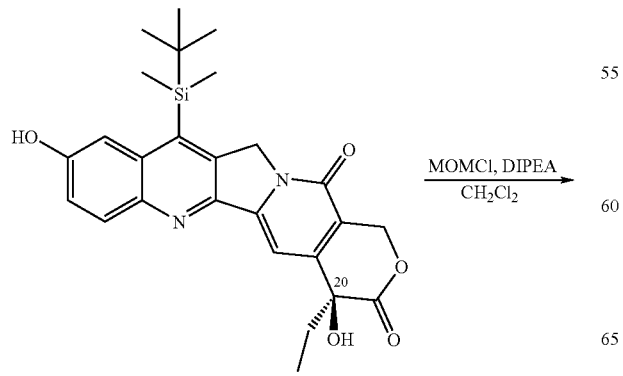

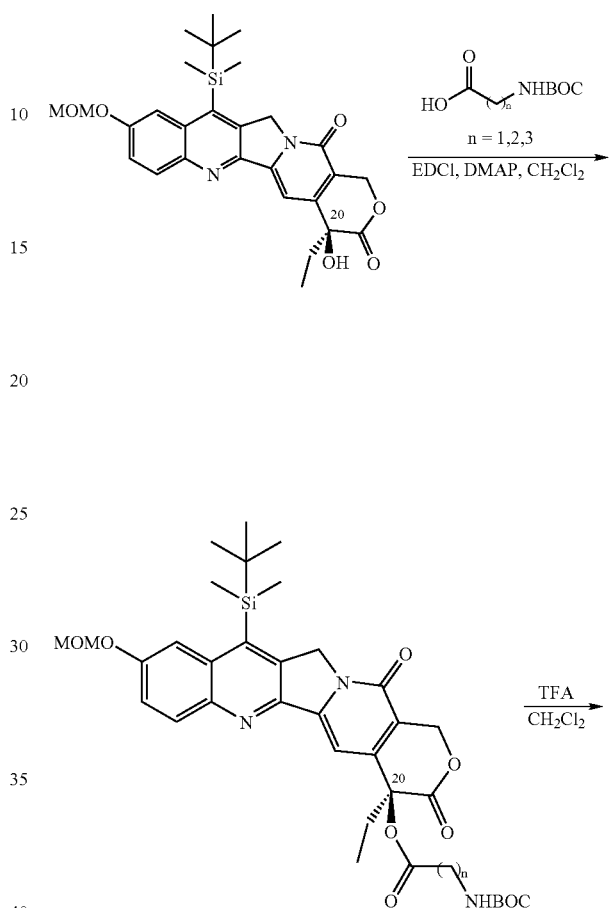

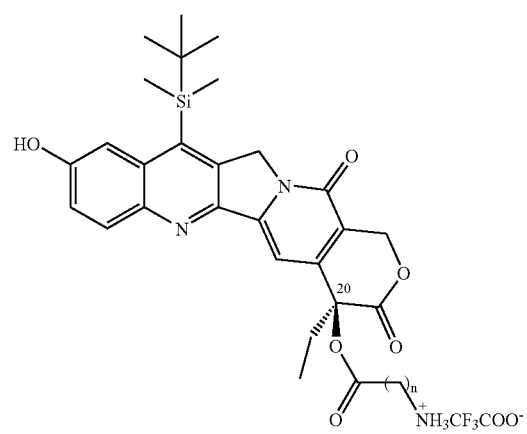

DB-67 (1 equiv) was dissolved in anhydrous dichloromethane, and DIPEA (5 equiv) was added under nitrogen atmosphere. The reaction mixture was stirred for 10 min at room temperature followed by the addition of MOMCl (5 equiv). The resulting solution was left stirring overnight. The reaction was terminated. Then the reaction mixture was diluted by dichloromethane and washed several times with water, dried ($MgSO_4$), filtered, and concentrated. Purification by chromatography on silica gel gave 10-MOM protected compound.

1-Ethyl-3-(3-dimethylaminopropyl)carbodiimide (EDCI, 3 equiv) was slowly added to a solution of 10-MOM protected compound (1 equiv), N-tert-butoxycarbonylamino acid (3 equiv) and 4-(Dimethylamino)pyridine (DMAP, 0.6 equiv) and anhydrous dichloromethane, which had been pre-cooled to 0° C. The resulting solution was allowed to warm to room temperature and stirred overnight. The organic fraction was washed with HCl (0.1 N) and water and then extracted several times with $CH_2Cl_2$. Organic layers were combined and dried with $MgSO_4$, followed by filtration and concentration. Purification of this residue by flash chromatography on silica gel gave chloromethyl methyl ether (MOM) and N-BOC protected prodrug. Deprotection of MOM and N-BOC groups was achieved simultaneously by stirring MOM and N-BOC protected prodrug in dichloromethane and trifluoroacetic acid for 30 minutes at room temperature, followed by concentration under high vacuum and recrystalization in methanol and ethyl ether. Purity of final products was determined by HPLC and prodrug purity was found to be greater than 98% pure.

EXAMPLE 2

Synthesis of DB-67 20-O-ester of N-methylglycine, mono (trifluoroacetate)

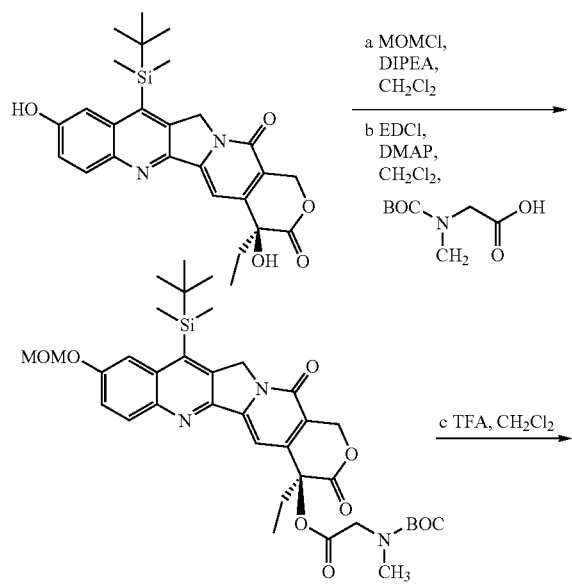

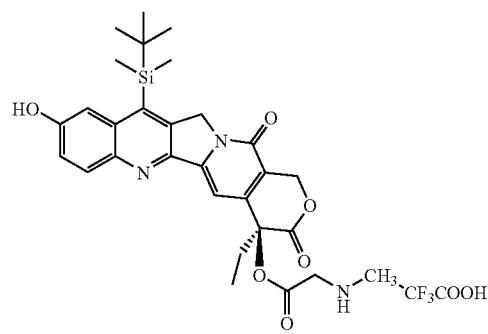

A solution of 7-t-butyldimethylsilyl-10-MOM-hydroxy-20(s)-CPT (100 mg, 0.19 mmol), N-(tert-butoxycarbonyl) metylyglycine (90 mg, 0.48 mmol) and DMAP (14 mg, 0.12 mmol) in 10 ml anhydrous dichloromethane was cooled to 0° C., followed by the addition of EDCI (110 mg, 0.57 mmol). The reaction mixture was allowed to come to room temperature and monitored by TLC. The resulting solution was washed with HCl (5 ml, 0.1 N) and water, then extracted with dichloromethane. The organic layer was dried with $MgSO_4$, then filtered and concentrated. Purification by column chromatography on silica gel ($CH_2Cl_2$—$CH_3COCH_3$, 95:5) gave yellow solid (120 mg, 90%). $^1$HNMR (400 MHz, $CDCl_3$): 0.70 (s, 6H), 1.01 (m, 12H), 1.45 (d, J=4.8, 9H), 2.10–2.34 (m, 2H), 2.96 (s, 3H), 3.54 (s, 3H), 4.05–4.31 (AB system, 2H), 5.27 (m, 2H), 5.32 (s, 2H), 5.37–5.42 (A of AB system, 1H), 5.68–5.72 (B of AB system, 1H), 7.13, 7.30 (ss, 1H), 7.46–7.51 (m, 1H), 7.91–7.94 (dd, J=6.4, J=2.4, 1H), 8.05–8.16 (dd, J=32.8, J=9.2, 1H). 7-t-butyldimethylsilyl-10-MOM-hydroxy-20(s)-CPT-20-O-ester of N-tert-butoxycarbonylmethyglycine (100 mg, 0.14 mmol) were dissolved in dichloromethane and trifluoroacetic acid, then stirred 30 min. at room temperature. The yellow solution was concentrated under high vacuum. Recrystalization by methanol and ethyl ether obtained yellow solid 86 mg, yield 90%. $^1$HNMR (400 MHz, CD30D): 0.73 (s, 6H), 1.02 (s, 9H), 1.08 (t, J=7.2, 1H), 4.27–4.40 (q, J=16.8, 2H), 5.35 (s, 2H), 5.47–5.51 (A of AB system, 1H), 5.63–5.67 (B of AB system, 1H), 7.34 (s, IH), 7.42–7.45 (dd, J=9.2, J=1.2, 1H), 7.67 (d, J=2.8, 1H), 8.19 (d, J=9.2, 1H).

EXAMPLE 3

Conversion of DB-67 20(S) ω-aminoalkanoanic esters to lactam, ortho lactone and acetic acid prodrugs

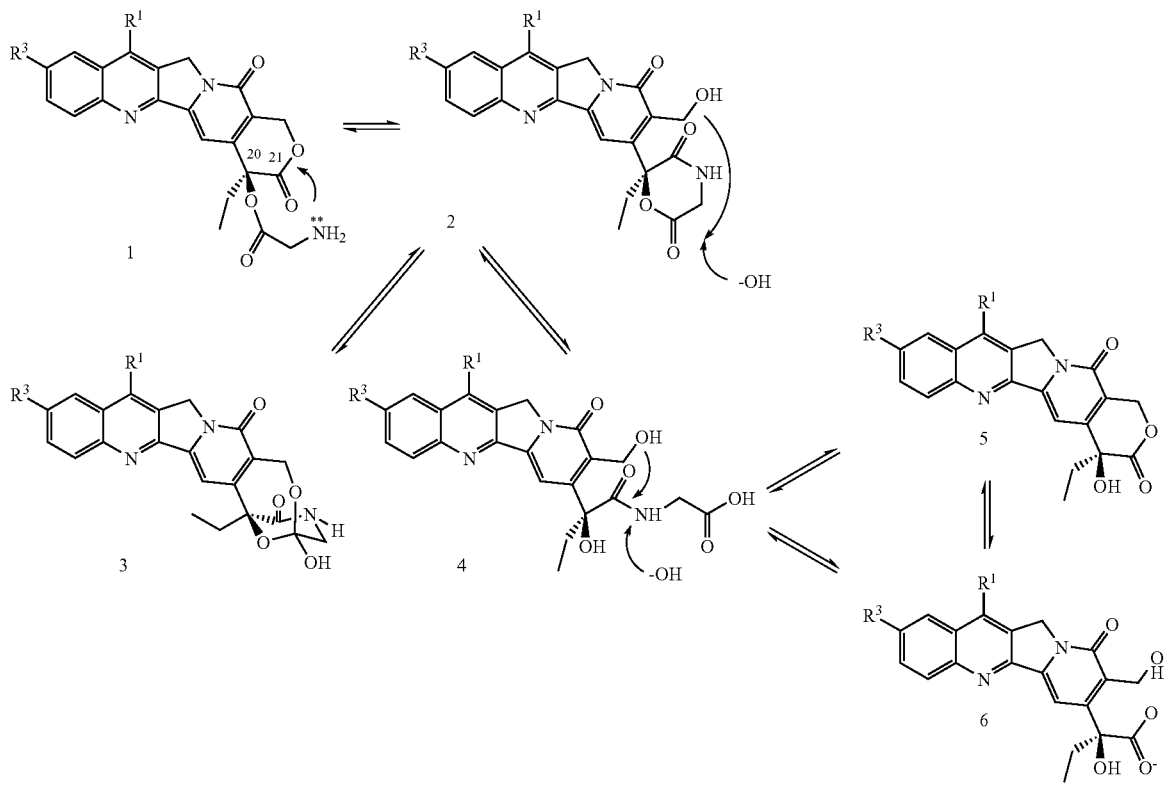

Glycinate Ester of DB-67: $R^1 = Si(CH_3)_2C(CH_3)_3$, $R^3 = OH$

At physiological pH of 7 or above, the nucleophilicity of the amine group of DB-67 20(S)-glycinate ester manifests itself and cyclization to the C-21 carbonyl carbon occurs. This cyclization triggers a rapid and convenient non-enzymatic decomposition process that releases active DB-67. DB-67 20(S)-glycinate 1 decomposed to produce several products: the closed-ring lactone form of DB-67 5, the ring-opened carboxylate form of DB-67 6, and two novel decomposition products 3 and 4 generated following the formation of an unusual six membered morpholine 2,5-dione ring 2 (or lactam intermediate). The lactam intermediate arose by intramolecular nucleophilic attack of the amino group on the lactone E-ring carbonyl carbon of DB-67 and is in fast equilibrium with structures 3 (which we refer to as the ortho lactone) and 4. Ortho lactone 3 arose by a second intramolecular reaction within the lactam intermediate and 3 exhibited the same mass as DB-6 20(S)-glycinate ester but with a strikingly different fragmentation pattern. 4 arose by a competitive intermolecular reaction to the lactam intermediate and reacted to release both 5 and 6. ESI/MS/MS showed that DB-67 glycinate ester fragmentation pattern [m/z(%)] was: 536 (100%), 461 (50%), 433 (20%); DB-67 ortho lactone fragmentation pattern was: 536 (100%), 518 (10%).

EXAMPLE 4

Procedure for the isolation of the ortho lactone from N-methyl DB-67 glycinate ester N-methyl DB-67 glycinate trifluoroacetic acid salt was dissolved in DMF, 1.2 eq. triethylamine was then added and reaction stirred overnight at room temperature. Organic solvent was removed and a yellow precipitate was rinsed with water, filtered, and dried under vacuum. Yield: 98%.

EXAMPLE 5

Loading of Compounds of Present Invention into Liposomes

Remote "active" loading of prodrug into premade small unilamellar vesicles, with diameters of 100 nm, was carried out by using transmembrane ammonium sulfate gradients. Prodrug was added to a liposomal suspension where initially $[(NH_4)_2SO_4]_{CORE} \cdot [(NH_4)_2SO_4]_{EXTERNAL}$; loading of the prodrug occurred as a result of base exchange (initiated by $NH_3$ gas molecules departing the liposome). Whereas underivatized camptothecin and DB-67 localize predominantly in the bilayer compartment of the liposome, their 20-OR prodrugs, where R) CO[CH$_2$]$_n$NH 2 and n) 1–3, loaded with high efficiency (60 to 90%) into the core of liposomes at clinically relevant drug-to-lipid ratios (between 1:4 to 1:20). More importantly, these core-loaded liposomal formulations of camptothecin 4-aminobutanoate ester and DB-67 4-aminobutanoate ester exhibited markedly improved stabilities in whole blood relative to their free forms. Whereas the decomposition of free prodrug in both cases was extensive, liposomal entrapment prevented the degradation process from occurring, providing indirect evidence that the prodrug was effectively retained within the liposome for periods up to 40 h. These time periods are known to be sufficient for successful tumor-targeting to be achieved.

What is claimed is:

1. A compound having the formula:

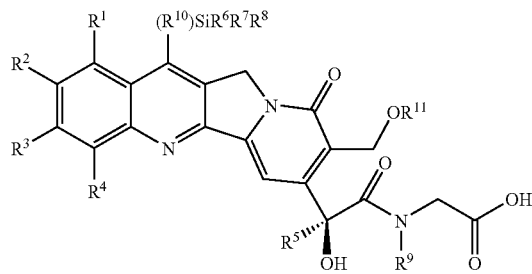

wherein $R^1$ and $R^2$ are independently the same or different and are hydrogen, an alkyl group, an alkenyl group, an alkynyl group, an alkoxy group, a phenoxy group, a napthyloxy group, an acyloxy group, OC(O)OR$^{12}$ wherein R$^{12}$ is an alkyl group, a carbamoyloxy group, a halogen, a hydroxy group, a nitro group, a cyano group, an azido group, a formyl group, a hydrazino group, C(O)R$^{13}$ wherein R$^{13}$ is an alkyl group, an alkoxy group, an amino group or a hydroxy group, SR$^{14}$, wherein R$^{14}$ is hydrogen, C(O)R$^{13}$, an alkyl group, a phenyl group or a napthyl group; R$^3$ is H, a nitro group, a halogen atom, an amino group, a hydroxy group, or a cyano group; R$^4$ is H, F, an alkyl group, an alkenyl group, an alkynyl group, a trialkylsilyl group or an alkoxy group; R$^5$ is a C$_{1-15}$ alkyl group, an allyl group, a benzyl group or a propargyl group; R$^6$, R$^7$ and R$^8$ are independently a C$_{1-15}$ alkyl group, a C$_{2-15}$ alkenyl group, a C$_{2-15}$ alkynyl group, a phenyl group, a napthyl group or a (CH$_2$)$_q$R$^{15}$ group, wherein q is an integer between 1 and 15 and R$^{15}$ is a hydroxy group, alkoxy group, an amino group, an alkylamino group, a dialkylamino group, a halogen atom, a cyano group or a nitro group; R$^9$ is a hydrogen, an alkyl group, an alkenyl group, an alkynyl group, an alkoxy group, a phenoxy group, a napthyloxy group, or an acyloxy group; R$^{10}$ is an alkylene group, an alkenylene group or an alkynylene group; R$^{11}$ is hydrogen, an alkyl group, an alkenyl group and (CH$_2$)$_L$NR$^{16}$R$^{17}$ wherein L may be an integer ranging from 1–30 and R$^{16}$ and R$^{17}$ are independently the same or different and are hydrogen, a C$_{1-15}$ alkyl group, a C$_{2-15}$ alkenyl group, a C$_{2-15}$ alkynyl group, a phenyl group, a napthyl group, a (CH$_2$)$_Y$R$^{18}$ group, a (CH$_2$)$_Y$C(O)R$^{18}$ group or a (CH$_2$)$_Y$CO$_2$R$^{18}$ wherein Y may be an integer ranging from 1 to 15 and R$^{18}$ is a hydroxy group, a thiol group, an alkylthiol, a silyl group, an alkoxy group, an amino group, an alkylamino group, a dialkylamino group, a halogen atom, a cyano group, a nitro group.

2. A compound having the formula:

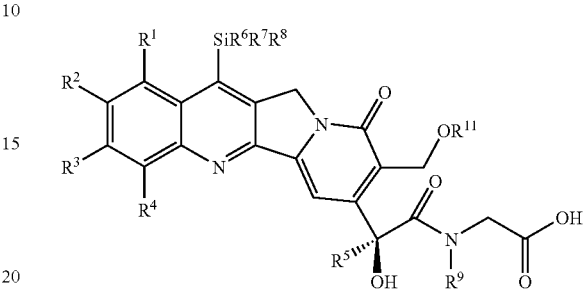

wherein $R^1$ and $R^2$ are independently the same or different and are hydrogen, an alkyl group, an alkenyl group, an alkynyl group, an alkoxy group, a phenoxy group, a napthyloxy group, an acyloxy group, OC(O)OR$^{12}$ wherein R$^{12}$ is an alkyl group, a carbamoyloxy group, a halogen, a hydroxy group, a nitro group, a cyano group, an azido group, a formyl group, a hydrazino group, C(O)R$^{13}$ wherein R$^{13}$ is an alkyl group, an alkoxy group, an amino group or a hydroxy group, SR$^{14}$, wherein R$^{14}$ is hydrogen, C(O)R$^{13}$, an alkyl group, or a phenyl group, a napthyl group; R$^3$ is H, a nitro group, a halogen atom, an amino group, a hydroxy group, or a cyano group; R$^4$ is H, F, an alkyl group, an alkenyl group, an alkynyl group, a trialkylsilyl group or an alkoxy group; R$^5$ is a C$_{1-15}$ alkyl group, an allyl group, a benzyl group or a propargyl group; R$^6$, R$^7$ and R$^8$ are independently a C$_{1-15}$ alkyl group, a C$_{2-15}$ alkenyl group, a C$_{2-15}$ alkynyl group, a phenyl group, a napthyl group or a (CH$_2$)$_q$R$^{15}$ group, wherein q is an integer between 1 and 15 and R$^{15}$ is a hydroxy group, alkoxy group, an amino group, an alkylamino group, a dialkylamino group, a halogen atom, a cyano group or a nitro group; R$^9$ is a hydrogen, an alkyl group, an alkenyl group, an alkynyl group, an alkoxy group, a phenoxy group, a napthyloxy group, or an acyloxy group; R$^{11}$ is hydrogen, an alkyl group, an alkenyl group and (CH$^2$)$_L$NR$^{16}$R$^{17}$ wherein L may be an integer ranging from 1–30 and R$^{16}$ and R$^{17}$ are independently the same or different and are hydrogen, a C$_{1-15}$ alkyl group, a C$_{2-15}$ alkenyl group, a C$_{2-15}$ alkynyl group, a phenyl group, a napthyl group, a (CH$_2$)$_Y$R$^{18}$ group, a (CH$_2$)$_Y$C(O)R$^{18}$ group or a (CH$^2$)$_Y$CO$_2$R$^{18}$ wherein Y may be an integer ranging from 1 to 15 and R$^{18}$ is a hydroxy group, a thiol group, an alkylthiol, a silyl group, an alkoxy group, an amino group, an alkylamino group, a dialkylamino group, a halogen atom, a cyano group, a nitro group.

* * * * *